United States Patent
Bessard et al.

[11] Patent Number: 5,869,667
[45] Date of Patent: Feb. 9, 1999

[54] PROCESS FOR PREPARING 2-PYRIMIDINECARBOXYLATES

[75] Inventors: Yves Bessard, Sierre; Gerhard Stucky, Brig-Glis, both of Switzerland

[73] Assignee: Lonza AG, Gampel/Valais, Switzerland

[21] Appl. No.: 891,787

[22] Filed: Jul. 14, 1997

[30] Foreign Application Priority Data

Jul. 18, 1996 [CH] Switzerland .................. 1797/96

[51] Int. Cl.⁶ ................. C07D 239/52; C07D 239/32; C07D 239/28
[52] U.S. Cl. ........................................ 544/319
[58] Field of Search ................................ 544/319

[56] References Cited

FOREIGN PATENT DOCUMENTS

| | | |
|---|---|---|
| 0152286 | 8/1985 | European Pat. Off. . |
| 0282266 | 9/1988 | European Pat. Off. . |
| 0582288 | 2/1994 | European Pat. Off. . |
| 2341925 | 3/1975 | Germany . |
| 3826230 | 2/1990 | Germany . |

OTHER PUBLICATIONS

*Neunhoffer, H., and G. Werner, Liebigs Ann. Chem.,* (1974), 1190–1194.
*Chemical Abstact,* vol. 125, No. 3, (Jul. 15, 1996), 125:33323k.
*Eilingsfeld, H. et al., Chem. Ber.,* (1968), 101, 2426–2434.
*Neunhoeffer, H., and G. Werner, Liebigs Ann. Chem.,* (1974), 1190–1194.
*Eilingsfeld, H., et al., Chem. Ber.,* (1968), 101, 2426–2434.

Primary Examiner—John M. Ford
Attorney, Agent, or Firm—Fisher, Christen & Sabol

[57] ABSTRACT

A process for preparing 2-pyrimidinecarboxylates of the general formula:

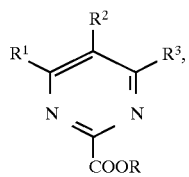

wherein R is $C_{1-6}$-alkyl, $C_{3-6}$-cycloalkyl, aryl or arylalkyl, and $R^1$ to $R^3$ are, independently of one another, hydrogen, $C_{1-6}$-alkyl, fluorinated $C_{1-6}$-alkyl, $C_{1-6}$-alkoxy, ($C_{1-6}$-alkoxy)-$C_{1-6}$-alkyl or ($C_{1-6}$-alkoxy)carbonyl. These are obtained from the corresponding 2-halopyrimidine, the corresponding alcohol ROH and carbon monoxide in the presence of a palladium/phosphine complex and a base. 2-pyrimidinecarboxylates are intermediates for preparing herbicides.

17 Claims, No Drawings

PROCESS FOR PREPARING 2-PYRIMIDINECARBOXYLATES

BACKGROUND OF THE INVENTION

1. Field of the Invention

The invention relates to a process for preparing substituted 2-pyrimidinecarboxylates by reacting 2-halopyrimidines with carbon monoxide and an alcohol in the presence of a catalyst and a base. The esters which can be prepared according to the invention have the general formula:

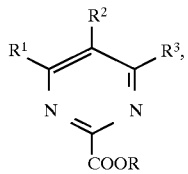

wherein:

R is $C_{1-6}$-alkyl, $C_{3-6}$-cycloalkyl, aryl or arylalkyl, and
$R^1$ to $R^3$ are, independently of one another, hydrogen, $C_{1-6}$-alkyl, fluorinated $C_{1-6}$-alkyl, $C_{1-6}$-alkoxy, ($C_{1-6}$-alkoxy)-$C_{1-6}$-alkyl or ($C_{1-6}$-alkoxy)carbonyl.

2. Background Art

Compounds having the structure of formula I are intermediates for the preparation of herbicides (European Published Patent Application No. 0152286 and German Published Patent Document No. 3,836,230) or pharmaceutically active ingredients (German Published Patent Document No. 2,341,925). Known syntheses of these compounds proceed, for example, from the corresponding 2-methylpyrimidines, whose methyl group is oxidized to form the carboxyl group with potassium permanganate and is then esterified [see, for example, H. Neunhoeffer and G. Werner, Liebigs *Ann. Chem.*, (1974), 1190–1194]. The synthesis of the compounds in which $R^1=R^3=$alkoxy normally proceeds from the propanediimidates obtainable from malonic dinitrile and alcohols and the monoxalate chlorides [H. Eilingsfeld et al., *Chem. Ber.*, (1968), 101, 2426–2434].

BROAD DESCRIPTION OF THE INVENTION

An object of the invention is to provide an alternative process which proceeds from readily accessible educts and provides high yields. Other objects and advantages of the invention are set out herein or are obvious herefrom to one skilled in the art.

The objects of the invention are achieved by the process of the invention.

The invention involves a process for preparing 2-pyrimidinecarboxylates of the general formula:

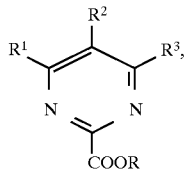

wherein R is $C_{1-6}$-alkyl, $C_{3-6}$-cycloalkyl, aryl or arylalkyl, and $R^1$ to $R^3$ are, independently of one another, hydrogen, $C_{1-6}$-alkyl, fluorinated $C_{1-6}$-alkyl, $C_{1-6}$-alkoxy, ($C_{1-6}$-alkoxy)-$C_{1-6}$-alkyl or ($C_{1-6}$-alkoxy)carbonyl. In the invention process, a 2-halopyrimidine of the general formula:

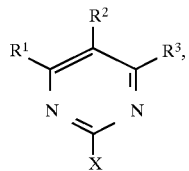

wherein $R^1$ to $R^3$ have the above-mentioned meanings and X is chlorine or bromine, is reacted directly with carbon monoxide and an alcohol of the general formula:

$$R\text{—}OH \qquad III,$$

wherein R has the above-mentioned meaning, in the presence of a base to form the desired product (I) in good yield if a palladium/phosphine complex is used as the catalyst.

Herein, $C_{1-6}$-alkyl is to be understood as meaning all linear and branched primary, secondary or tertiary alkyl groups containing up to 6 carbon atoms. Correspondingly, $C_{1-6}$-alkoxy and ($C_{1-6}$-alkoxy)carbonyl are to be understood as meaning the ether and ester functions made up of $C_{1-6}$-alkyl and oxygen or oxygen and carbonyl and, analogously thereto, ($C_{1-6}$-alkoxy)-$C_{1-6}$-alkyl is to understood as meaning the alkoxyalkyl groups formed by replacing a hydrogen atom in $C_{1-6}$-alkyl by $C_{1-6}$-alkoxy, for example, methoxymethyl or ethoxymethyl.

Herein, aryl is to be understood as meaning, in particular, monocyclic or polycyclic systems, for example, phenyl, naphthyl, biphenylyl or anthryl. These cyclic systems may carry one or more identical or different substituents, for example, low alkyl groups, such as methyl, halogenated alkyl groups, such as trifluoromethyl, low alkoxy groups, such as methoxy, or low alkylthio (alkanesulfanyl) or alkanesulfonyl groups, such as methylthio or ethanesulfonyl. Substituted phenyl is to be understood as meaning, in particular, groups such as fluorophenyl, methoxyphenyl, tolyl or trifluoromethylphenyl, the substituents preferably being located in the para-position. Correspondingly, arylalkyl is to be understood as meaning the groups formed from low alkyl groups, in particular $C_{1-6}$-alkyl, by replacing a hydrogen atom by one of the aryl groups defined above.

DETAILED DESCRIPTION OF THE INVENTION

The 2-halopyrimidines (II) which serve as the starting material are known compounds or can be prepared analogously to known compounds. A process for preparing 2-halo-4,6-dialkoxypyrimidines is described, for example, in European Published Patent Application No. 0582288. Preferably, the 2-chloropyrimidines (X is Cl) are used as 2-halopyrimidines.

$C_{1-4}$-alkylesters (R is $C_{1-4}$-alkyl) prepared by the process according to the invention by using the corresponding $C_{1-4}$-alkanol as alcohol (III), are preferred. Particularly preferred are methyl, ethyl and isopropyl esters.

Also preferred is the preparation of 2-pyrimidinecarboxylates (I) which are unsubstituted in position 5 of the pyrimidine ring ($R^2$ is H).

Particularly preferred is the preparation of 2-pyrimidinecarboxylates (I) which carry hydrogen, $C_{1-4}$-alkoxy groups, ($C_{1-4}$-alkoxy)carbonyl groups or ($C_{1-4}$-alkoxy)methyl groups in positions 4 and 6 of the pyrimidine ring ($R^1$, $R^3$).

A tertiary phosphine is advantageously used as the phosphine in the catalytically active palladium/phosphine complex. Suitable, for example, are triarylphosphines, such as triphenylphosphine or triphenylphosphines substituted on the phenyl groups, or diarylphosphines in which the third valency on the phosphorus is occupied by another organic radical, for example, an aliphatic chain or a metallocenyl system. Diphosphines are preferably used which have the general formula:

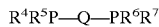

$$R^4R^5P\text{—}Q\text{—}PR^6R^7 \qquad \text{IV},$$

wherein $R^4$ to $R^7$ are, independently of one another, optionally substituted phenyl, $C_{1-6}$-alkyl or $C_{3-6}$-cycloalkyl and Q is a 1,1'-ferrocenediyl group or a group of the formula —$[CH_2]_n$—, where n is 3 or 4.

The catalytically active palladium/phosphine complex is advantageously formed in situ by reacting palladium in finely divided elemental form (for example, palladium on active carbon), a Pd(II) salt (for example, the chloride or the acetate) or a suitable Pd(II) complex [for example, dichlorobis(triphenylphosphine)palladium(II)] with the phosphine. Particularly preferred are palladium(II) acetate and dichlorobis(triphenylphosphine)palladium(II). The palladium is preferably used in an amount of 0.02 to 2 mol percent Pd(II) or 0.5 to 5 mol percent Pd(O) (as Pd/C), in each case relative to the halogen compound (II). The phosphine is advantageously used in excess (relative to Pd), preferably in an amount of 0.2 to 10 mol percent, also relative to the halogen compound (II).

The alcohol (III) may also simultaneously serve as a solvent. Optionally, an additional solvent may be used. Suitable as additional solvents are both relatively nonpolar solvents, for example, toluene or xylene, and polar solvents, for example, acetonitrile, tetrahydrofuran or N,N-dimethylacetamide.

Preferably, a weak base selected from the group comprising the alkali or alkaline earth salts of low carboxylic acids, the alkali or alkaline earth hydrogencarbonates or the alkali or alkaline earth (di)hydrogenphosphates, is used as the base. Particularly preferred are alkali acetates, in particular sodium acetate and potassium acetate.

The reaction temperature is preferably 80° to 250° C. The carbon monoxide pressure is preferably 1 to 50 bar.

The reaction time depends, inter alia, on the temperature, the reactivity of the compounds used and the concentration ratios and is typically in the range of a few hours. Since subsequent reactions may occur in the case of an excessively long reaction time, the reaction process is advantageously monitored with a suitable analytical method (for example, GC) and the reaction terminated after reaching the maximum product concentration.

The following examples illustrate the performance of the process according to the invention.

EXAMPLE 1

Methyl 4,6-dimethoxy-2-pyrimidinecarboxylate
(I, R=Me, $R^1$=$R^3$=OMe, and $R^2$=H)

3.49 g (20 mmol) of 2-chloro-4,6-dimethoxypyrimidine (prepared according to European Published Patent Application No. 0582288), 256 mg (0.6 mmol) of 1,4-bis (diphenylphosphino)butane, 28 mg (40 μmol) of dichlorobis (triphenylphosphine)palladium(II), 4.92 g (60 mmol) of sodium acetate, 1.92 g (60 mmol) of methanol and 56 ml of tetrahydrofuran were introduced into an indirectly heated (oil bath) metal autoclave. The autoclave was flushed several times with carbon monoxide, then the carbon monoxide pressure was increased to 15 bar and the reaction mixture was heated for 6 hours at 180° C. bath temperature. A GC analysis of the reaction mixture revealed a yield of 99 percent with a conversion of 100 percent. For the purpose of working-up, the reaction mixture was evaporated down in vacuo and the residue chromatographed on silica gel 60 with hexane/ethyl acetate (1:1). The yield of isolated product was 1.0 g (71 percent) of colorless crystals. Other data concerning the product was:

M.p: 129.7°–131.1° C.
$^1$H NMR (CDCl$_3$) δ=6.15 (s, 1H); 4.03 (s, 6H); 4.00 (s, 3H).
MS (m/z): 198 (M$^+$); 197; 183; 168; 139; 125; 108; 93.

EXAMPLE 2

Methyl 4,6-dimethoxy-2-pyrimidinecarboxylate
(I, R=Me, $R^1$=$R^3$=OMe, and $R^2$=H)

The procedure was as described in Example 1, but 9.0 mg (40 μmol of palladium(II) acetate was used instead of dichlorobis(triphenylphosphine)-palladium(II) and 333 mg (0.6 mmol) of 1,1'-bis(diphenylphosphino)ferrocene was used instead of 1,4-bis(diphenylphosphino)butane. The bath temperature was 165° C. and the reaction time was 4 hours. A GC analysis of the reaction mixture revealed a yield of 92 percent with an equally large conversion. The yield of isolated product was 3.36 g (85 percent) of colorless crystals.

EXAMPLE 3

Methyl 4,6-dimethoxy-2-pyrimidinecarboxylate
(I, R=Me, $R^1$=$R^3$=OMe, and $R^2$=H)

The procedure was as described in Example 2, but the tetrahydrofuran was replaced by methanol (total amount: 50 ml) and the reaction time was reduced to 2 hours. A GC analysis of the reaction mixture revealed a quantitative yield and conversion. The yield of isolated product was 3.54 g (90 percent) of light beige crystals.

EXAMPLE 4

Methyl 4,6-dimethoxy-2-pyrimidinecarboxylate
(I, R=Me, $R^1$=$R^3$=OMe, and $R^2$=H)

The procedure was as described in Example 3, but the 1,1'-bis(diphenylphosphino)ferrocene was replaced by 163 mg (0.6 mmol) of triphenylphosphine. The reaction time was 4 hours at 170° C. bath temperature. A GC analysis of the reaction mixture revealed a yield of 42 percent (in addition to 58 percent of unconverted starting material).

EXAMPLE 5

Methyl 4,6-dimethoxy-2-pyrimidinecarboxylate

The procedure was as described in Example 4, but the triphenylphosphine was replaced by 211 mg (0.6 mmol) of tris(4-methyoxyphenyl)phosphine. A GC analysis of the reaction mixture revealed a yield of 62 percent (in addition to 38 percent of unconverted starting material).

EXAMPLE 6

Ethyl 4,6-dimethoxy-2-pyrimidinecarboxylate
(I, R=Et, $R^1$=$R^3$=OMe, and $R^2$=H)

The procedure was as described in Example 3, but 50 ml of ethanol was used instead of methanol. The reaction time was 2.5 hours at 160° C. bath temperature. A GC analysis of the reaction mixture revealed a yield of 95.5 percent (in addition to 4.5 percent of unreacted starting material). The yield of isolated product was 3.71 g (86.7 percent) of pale yellow crystals, content (GC) 99.2 percent. Other data regarding the product was:

M.p.: 55.9°–57.4° C.

$^1$H NMR (CDCl$_3$) δ=6.15 (s, 1H); 4.46 (q, 2H); 4.02 (s, 6H); 1.43 (t, 3H).

MS (m/z): 212 (M$^+$); 211; 183; 154; 140; 125.

EXAMPLE 7

Propyl 4,6-dimethoxy-2-pyrimidinecarboxylate
(I, R=i-Pr, R$^1$=R$^3$=OMe, and R$^2$=H)

The procedure was as described in Example 3, but 50 ml of isopropyl alcohol was used instead of methanol. The reaction time was 4 hours at 170° C. bath temperature. A GC analysis of the reaction mixture revealed a yield of 87 percent, with a conversion of 92 percent. The yield of isolated product was 2.46 g (54 percent) of greenish crystals, content (GC) 100 percent. Other data concerning the product was:

M.p.: 64.6°–66.6° C.

$^1$H NMR (CDCl$_3$) δ=6.15 (s, 1H); 5.28 (sept., 1H); 4.01 (s, 6H); 1.42 (d, 6H).

MS (m/z): 226 (M$^+$); 211; 183; 167; 140.

EXAMPLE 8

Cyclohexyl 4,6-dimethoxy-2-pyrimidinecarboxylate
(I, R=cyclohexyl, R$^1$=R$^3$=OMe, and R$^2$=H)

The procedure was as described in Example 3, but the methanol was replaced by 50 ml of cyclohexanol. The reaction time was 3 hours and the bath temperature was 160° C. The yield of isolated product was 4.08 g (75 percent) of light yellow crystals. Other data regarding the product was:

M.p.: 99.0°–101.2° C.

$^1$H NMR (CDCl$_3$) δ=6.15 (s, 1H); 5.07 (m, 1H); 4.01 (s, 6H); 2.0 (m, 2H); 1.8 (m, 2H); 1.6 (m, 3H); 1.4 (m, 3H).

MS (m/z): 266 (M$^+$); 221; 185; 167; 139.

EXAMPLE 9

Benzyl 4,6-dimethoxy-2-pyrimidinecarboxylate
(I, R=benzyl, R$^1$=R$^3$=OMe, and R$^2$=H)

The procedure was as described in Example 3, but the methanol was replaced by 4.33 g of benzyl alcohol and 50 ml of tetrahydrofuran. The reaction time was 3 hours and the bath temperature was 160° C. The yield of isolated product was 4.18 g (76 percent) of beige crystals. Other data regarding the product was:

M.p.: 96.8°–98.1° C.

$^1$H NMR (CDCl$_3$) δ=7.50 ("d", 2H); 7.45 (m, 3H); 6.15 (s, 1H); 5.43 (s, 2H); 4.01 (s, 6H).

MS (m/z): 274 (M$^+$); 246; 168; 140.

What is claimed is:

1. A process for preparing a 2-pyrimidinecarboxylate of formula:

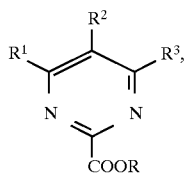

I wherein R is C$_{1-6}$-alkyl, C$_{3-6}$-cycloalkyl, aryl or arylalkyl, and R$^1$ to R$^3$ are, independently of one another, hydrogen, C$_{1-6}$-alkyl, fluorinated C$_{1-6}$-alkyl, C$_{1-6}$-alkoxy, (C$_{1-6}$-alkoxy)-C$_{1-6}$-alkyl or (C$_{1-6}$-alkoxy)carbonyl, comprising reacting a 2-halopyrimidine of formula:

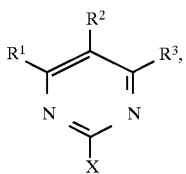

II wherein R$^1$ to R$^3$ have the above-mentioned meanings and X is chlorine or bromine, with carbon monoxide and an alcohol of formula:

R—OH    III, wherein R has the above-mentioned meaning, in the presence of a catalytically active palladium/phosphine complex and a base.

2. The process according to claim 1 wherein X is chlorine.

3. The process according to claim 2 wherein R is C$_{1-4}$-alkyl.

4. The process according to claim 3 wherein R$^2$ is hydrogen.

5. The process according to claim 4 wherein R$^1$ and R$^3$ are, independently of one another, hydrogen, C$_{1-4}$-alkoxy, (C$_{1-4}$-alkoxy)carbonyl or (C$_{1-4}$-alkoxy)methyl.

6. The process according to claim 5 wherein a diphosphine or formula:

R$^4$R$^5$P—Q—PR$^6$R$^7$    IV, wherein R$^4$ to R$^7$ are, independently of one another, phenyl, optionally substituted phenyl, C$_{1-6}$-alkyl or C$_{3-6}$-cycloalkyl and Q is a 1,1'-ferrocenediyl group or a group of the formula —[CH$_2$]$_n$—, wherein n is 3 or 4, is used as phosphine in the catalytically active palladium/phosphine complex.

7. The process according to claim 6 wherein the catalytically active palladium/phosphine complex is formed in situ from the phosphine and palladium(II) acetate or dichlorobis (triphenylphosphine)palladium(II).

8. The process according to claim 7 wherein a base selected from the group consisting of the alkali and alkaline earth salts of low carboxylic acids, the alkali and alkaline earth hydrogencarbonates and the alkali and alkaline earth (di)hydrogenphosphates, is used as the base.

9. The process according to claim 8 wherein an alkali acetate is used as the base.

10. The process according to claim 9 wherein sodium acetate or potassium acetate is used as the base.

11. The process according to claim 1 wherein R$^2$ is hydrogen.

12. The process according to claim 1 wherein R$^1$ and R$^3$ are, independently of one another, hydrogen, C$_{1-4}$-alkoxy, (C$_{1-4}$-alkoxy)carbonyl or (C$_{1-4}$-alkoxy)methyl.

13. The process according to claim 1 wherein a diphosphine of the formula:

R$^4$R$^5$P—Q—PR$^6$R$^7$    IV, wherein R$^4$ to R$^7$ are, independently of one another, phenyl, optionally substituted phenyl, C$_{1-6}$-alkyl or C$_{3-6}$-cycloalkyl and Q is a 1,1'-ferrocenediyl group or a group of the formula —[CH$_2$]$_n$—, wherein n is 3 or 4, is used as phosphine in the catalytically active palladium/phosphine complex.

14. The process according to claim 1 wherein the catalytically active palladium/phosphine complex is formed in situ from the phosphine and palladium(II) acetate or dichlorobis(triphenylphosphine)palladium(II).

15. The process according to claim 1 wherein a base selected from the group consisting of the alkali and alkaline earth salts of low carboxylic acids, the alkali and alkaline earth hydrogencarbonates and the alkali and alkaline earth (di)hydrogenphosphates, is used as the base.

17. The process according to claim 1 wherein sodium acetate or potassium acetate is used as the base.

16. The process according to claim 1 wherein an alkali acetate is used as the base.

* * * * *